United States Patent [19]
Demuth et al.

[11] 4,415,756
[45] Nov. 15, 1983

[54] PURE ENANTIOMERS OF BICYCLO[2.2.2]OCT-5-EN-2-ONES, PROCESSES FOR THEIR PRODUCTION AND THEIR USE

[75] Inventors: Martin Demuth; Kurt Schaffner, both of Mülheim, Fed. Rep. of Germany

[73] Assignee: Studiengesellschaft Kohle mbH, Mülheim/Ruhr, Fed. Rep. of Germany

[21] Appl. No.: 326,644

[22] Filed: Dec. 2, 1981

[30] Foreign Application Priority Data

Dec. 6, 1980 [DE] Fed. Rep. of Germany ....... 3046106

[51] Int. Cl.$^3$ ............................................. C07C 45/00
[52] U.S. Cl. .................................. 568/365; 568/361; 568/366; 568/374; 568/591; 568/373; 260/465 D; 560/118; 562/500
[58] Field of Search ............... 568/356, 365, 361, 366, 568/374; 260/465 D; 560/118; 562/500

[56] References Cited
PUBLICATIONS

Geivandov et al., Chem. Abst., vol. 95, #24354f, p. 631, (1981).
Torosyan et al., Chem. Abst., vol. 92, #58589q, p. 656, (1980).
Freeman et al., J. Org. Chem., vol. 33, pp. 2211–2214, (1968).
Alforo et al., Tetrahedron, vol. 30, pp. 559, (1974).
Lopatnik et al., Chem. Abst., vol. 95, #115149j, p. 666, (1981).
Monti et al., J. Org. Chem., vol. 43, pp. 4062–4069, (1978).
Mislow et al., J. Am. Chem. Soc., vol. 84, pp. 1956, (1962).

*Primary Examiner*—James H. Reamer
*Attorney, Agent, or Firm*—Sprung, Horn, Kramer & Woods

[57] ABSTRACT

New bicyclo[2.2.2]oct-5-en-2-ones of the formulae Ia and Ib in the form of pure enantiomers and processes for preparing them are described. The compounds are used for the preparation of pure enantiomers of the formula V by sensitized photoreaction or of compounds of the formula VI by unsensitized photoreaction.

8 Claims, No Drawings

PURE ENANTIOMERS OF BICYCLO[2.2.2]OCT-5-EN-2-ONES, PROCESSES FOR THEIR PRODUCTION AND THEIR USE

This invention relates to pure enantiomers of bicyclo[2.2.2]oct-5-en-2-ones, processes for producing them by complete or partial ketalization and separation of the product mixture by chromatography and distillation and the use of the enantiomeric bicyclo[2.2.2]oct-5-en-2-ones.

BACKGROUND OF THE INVENTION

P. K. Freeman, D. M. Balls and D. J. Brown, J. Org. Chem. 33, 2211 (1968) (see also the publications 10 and 15 cited in S. Ranganathan, D. Ranganathan and A. K. Mehrotra, Syntheses 1977, 289) already described the synthesis of racemic mixtures of bicyclo[2.2.2]oct-5-en-2-ones starting from substituted cyclohexa-1,4-dienes. Similarly, I. Alfaro, W. Ashton, K. L. Rabone & N. A. J. Rogers, Tetrahedron, 30, 559 (1974) and R. P. Gregson & R. N. Mirrington, Chem. Commun. 1973, 598, described substituted bicyclo[2.2.2]oct-5-en-2-ones using 2-acetoxy- or 2-chloroacrylonitriles as ene component.

The enrichment of an enantiomer has been described heretofore only by K. Mislow & J. G. Berger, Z. Am. Chem. Soc., 84, 1956 (1962) through recrystallization of ephedrine salts. This enrichment resulted in an about 40% optical purity.

The photochemical conversion of racemates of bicyclo[2.2.2]oct-5-en-2-ones to form racemic tricyclo-[3.3.0.0$^{2,8}$]octan-3-ones or bicyclo[4.2.0]octenones was described by R. S. Givens, W. F. Oettle, R. L. Coffin & R. G. Carlson, J. Am. Chem. Soc. 93, 3957 (1971). The photochemical conversion of racemates of bicyclo[2.2.2]oct-5-en-2-ones was also reported by C. Carter, S. Chandrasekhar, M. Demuth, K. Nakano & K. Schaffner in Contributed Paper No. 39 of the IUPAC VIII/1980 in Seefeld, Austria.

The racemic bicyclo[2.2.2]oct-5-en-2-ones having been described contain only H and one methyl group as substituents.

THE INVENTION

It is an object of the present invention to provide the technically important pure enantiomers of bicyclo[2.2.2]-oct-5-en-2-ones to achieve from these the access to the pure enantiomers of tricyclo[3.3.0.0$^{2,8}$]octanones and bicyclo[4.2.0]octenones.

Therefore, the invention relates to bicyclo[2.2.2]-oct-5-en-2-ones of the formulae Ia and Ib in the form of pure enantiomers:

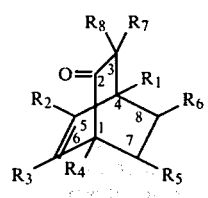

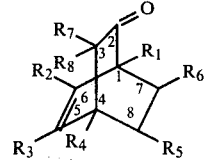

wherein $R_1$, $R_2$, $R_3$, $R_4$, $R_5$ and $R_6$ may be H, $C_1$–$C_8$-alkyl, $C_1$–$C_8$-alkoxyl and hydroxylated and/or carbonylated $C_1$–$C_8$-alkyl groups which may contan one or more double bonds and/or triple bonds, and may also be Cl, Br, F and CN as well as COOH and/or esters thereof and

(wherein R may be H, $C_1$–$C_8$-alkyl, $C_1$–$C_8$-alkoxyl and a hydroxylated and/or carbonylated $C_1$–$C_8$-alkyl group which may contain one or more double bonds and/or triple bonds and, moreover, the carbonyl group may be acetalized or ketalized), and $R_7$ and $R_8$ may be H, $C_1$–$C_8$-alkyl, $C_1$–$C_8$-alkoxyl and hydrolylated and/or carbonylated $C_1$–$C_8$-alkyl groups which may contain one or more double bonds and/or triple bonds.

It is another object of the invention to provide a process for the production of pure enantiomers of bicyclo[2.2.2]oct-5-en-2-ones of the formulae Ia and Ib wherein $R_1$, $R_2$, $R_3$, $R_4$, $R_5$, $R_6$, $R_7$ and $R_8$ are as defined above by Diels-Alder addition of cyclohexadienes of the formulae II and III

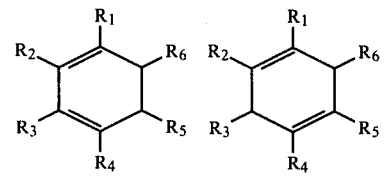

wherein $R_1$, $R_2$, $R_3$, $R_4$, $R_5$ and $R_6$ are as defined above with enes of the formula

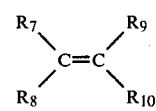

wherein $R_7$ and $R_8$ are as defined above and $R_9$ and $R_{10}$ are hydrolyzable substituents such as halogens, —C≡N,

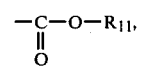

—$OR_{11}$, $NO_2$ or amines, wherein $R_{11}$ is an alkyl group having 1 to 4 carbon atoms, the process being characterized in that the racemates of the bicyclo[2.2.2]oct-5-en-2-ones obtained by Diels-Alder addition are either completely ketalized with pure enantiomers of diols and the ketals are separated by chromatography or, in case of only partial ketalization, the enantiomeric bicyclo[2.2.2]oct-5-en-2-one which has not or less been ketalized is separated from the ketalized enantiomer(s) by distillation and/or chromatography and the latter are also separated by chromatography.

It is another object of the invention to provide a process for the regioselective production of bicyclo[2.2.2]oct-5-en-2-ones of the formula I wherein $R_1$, $R_2$, $R_3$, $R_4$, $R_5$, $R_6$, $R_7$ and $R_8$ are as defined above by Diels-Alder addition of cyclohexadienes of the formula II and III wherein $R_1$, $R_2$, $R_3$, $R_4$, $R_5$ and $R_6$ are as defined above with enes of the Formula IV wherein $R_7$ and $R_8$ are as defined above and $R_9$ and $R_{10}$ are hydrolyzable substituents such as halogens, —C≡N,

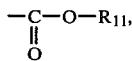

—$OR_{11}$, $NO_2$ amines, wherein $R_{11}$ is an alkyl group having 1 to 4 carbon atoms, the process being characterized in that the Diels-Alder addition is carried out in the temperature range of 60° to 120° C. or in the temperature range of 140° to 200° C. in the presence of polymerization inhibitors such as, for example, hydroquinone.

It is another object of the invention to use the compounds according to claim 1 for the production of pure enantiomers of the formula V by the sensitized photoreaction and of compounds of the formula VI by the unsensitized photoreaction.

The $C_1$–$C_8$-alkyl, $C_1$–$C_8$-alkoxyl and the hydroxylated and carbonylated $C_1$–$C_8$-alkyl groups are straight-chain and branched alkyl groups.

Specific examples of groups $C_1$–$C_8$ in $R_1$ to $R_8$ and in R include H, methyl, ethyl, iso- and n-propyl, n-1-butyl, n-2-butyl, isobutyl, t-butyl. Preferred of the $C_5$–$C_8$-alkyl, alkoxyl and hydroxylated and carbonylated alkyl groups are the n-alkyl groups and the 2- and 3-methyl-alkyl groups. The double bonds, triple bonds, OH groups and C=O groups in the $C_2$–$C_8$-alkyl, alkoxyl and hydroxylated and carbonylated alkyl groups are preferably in 1-, 2- and 3-position.

Thus, the object has been accomplished by either completely ketalizing the racemic mixtures of the bicyclo[2.2.2]oct-5-en-2-ones recovered by Diels-Alder addition of cyclohexadienes followed by chromatographic separation of the ketals or by ketalizing them only partially. The non-ketalized enantiomer was then either separated by distillation followed by chromatographic separation of the ketals having been formed or the mixture of non-ketalized and ketalized enantiomers was separated by chromatography without a distillation step. It has been found surprisingly that both optical antipodes of the bicyclo[2.2.2]oct-5-en-2-ones could be recovered in pure form by separating by chromatography the ketals which have been obtained by reacting the bicyclo[2.2.2]oct-5-en-2-ones with optically pure diols. Suitable diols include those which contain the OH groups in vicinal position or in 1,3-position such as, for example, butane-2,3-diols, pentane-2,4-diols, but especially L(+) and D(—)-tartaric acid and esters thereof.

It has further been found surprisingly that the ketalization can be controlled to a great extent by the selection of the substituents on the diol used, the selection of the ester groups of the tartaric acid esters and the selection of the substituents on the bicyclo[2.2.2]oct-5-en-2-one and the degree of reaction.

Thus, ketalization of racemic 1-methyl-1-bicyclo[2.2.2]oct-5-en-2-one with L(+) ethyl tartrate results in preferred ketalization of (—)-1-methyl-bicyclo[2.2.2]oct-5-en-2-one in a ratio of 1:0.4 as compared with (+)-1-methyl-bicyclo[2.2.2]oct-5-en-2-one. When using as ketalization agent L(+)-diisopropyltartrate, substantially only the (—)-1-methyl-bicyclo[2.2.2]oct-5-en-2-one is ketalized with a 50% conversion while (+)-1-methyl-bicyclo[2.2.2]oct-5-en-2-one remains almost unchanged and can be distilled off.

Further preferred esters are phenyl and methyl esters.

To produce the racemic bicyclo[2.2.2]oct-5-en-2-ones, there are useful 1,4-cyclohexadienes and 1,3-cyclohexadienes in which the substituents $R_1$, $R_2$, $R_3$, $R_4$, $R_5$ and $R_6$ may be H, $C_1$–$C_8$-alkyl, $C_1$–$C_8$-alkoxyl and hydroxylated and carbonylated $C_1$–$C_8$-alkyl groups which may contain one or more double bonds and/or triple bonds and may also be Cl, Br, F and CN as well as COOH and/or esters thereof and/or COR (wherein R may be H, $C_1$–$C_8$-alkyl, $C_1$–$C_8$-alkoxyl and hydroxylated and/or carbonylated $C_1$–$C_8$-alkyl groups which may contain one or more double bonds and/or triple bonds and, moreover, the carbonyl group may be acetalized and ketalized, respectively). As ene component, use is made of the olefin according to formula IV wherein $R_7$ and $R_8$ are as defined above and $R_9$ and $R_{10}$ are hydrolyzable substituents such as halogens, —C≡N,

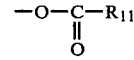

or —$OR_{11}$, $NO_2$ or amines, wherein $R_{11}$ is an alkyl group having 1 to 4 carbon atoms.

The Diels-Alder addition may be carried out under usual conditions. However, it has been found surprisingly that high regioselectivity of the addition may be achieved if specific temperature ranges are maintained. For example, if the addition of 1-methylcyclohexadiene and 2-chloroacrylonitrile as the ene component is carried out in the presence of polymerization inhibitors such as hydroquinone in the temperature range of 60° to 120° C. and preferably at 110° C., there is obtained a 5:1 mixture of the isomers 7 and 8. On the other hand, when operating in the temperature range of 140° to 200° C. and preferably at 150° C. the isomer 8 is obtained in pure form (7 = formula Ia with $R_1$ = methyl; 8 = formula Ib with $R_1$ = methyl).

Ketalization of the bicyclo[2.2.2]oct-5-en-2-ones with diols is carried out in usual manner in the presence of acids. The reaction may be effected both in solvents and also without solvents while continuously withdrawing advantageously the water which is formed during the reaction. The separation of the ketals is carried out by column chromatography but may also be effected by other chromatographic methods. Once the separation has been effected, the pure enantiomers of the bicyclo[2.2.2]oct-5-en-2-ones can be obtained by usual hydrolytic cleavage of the ketals.

If the pure enantiomers of the bicyclo[2.2.2]oct-5-en-2-ones are irradiated in the presence of sensitizers such as, for example, acetophenone, acetone, benzophenone or benzene, especially in a range of wave lengths of 254 to 400 nm, there is surprisingly obtained in a selective manner the corresponding pure enantiomer of tricyclo[3.3.0.0$^{2,8}$]-octan-3-one of the formula V. If a pure enantiomer of bicyclo[2.2.2]oct-5-en-2-one is irradiated without the addition of sensitizers, there is surprisingly obtained a pure enantiomeric bicyclo[4.2.0]octenone of the formula VI. Therefore, it is possible for the first time by the use of the pure enantiomer of bicyclo[2.2.2]oct-5-en-2-ones to recover these commercially valuable products selectively in an optically pure form by synthesis.

In order to illustrate the invention in greater detail, the following examples are given.

EXAMPLE 1

A mixture of 1-[pentenyl-3]-1,4-cyclohexadiene and 2-chloroacrylonitrile was heated for 10 hours at 120° C. in the presence of hydroquinone as polymerization inhibitor. The raw product was distilled at 71° to 73° C./0.13 millibars and the distillate was hydrolyzed in an aqueous solution of potassium hydroxide in dimethyl sulfoxide at 120° C. for 30 minutes. The mixture was then poured on ice. Extraction with pentane gave a racemic mixture of 4-[pentenyl-3]-bicyclo[2.2.2]oct-5-en-2-one in a yield of 58%.

(Analysis in %: Calculated: C, 82.11; H, 9.47; O, 8.42.
Found: C, 82.1; H, 9.5; O, 8.3).

EXAMPLE 2

A mixture of 1-methyl-1,4-cyclohexadiene and 2-chloroacrylonitrile was heated for 14 hours at 110° C. in the presence of hydroquinone as polymerization inhibitor. The raw product was distilled at 60° to 65° C./0.13 millibars and the distillate was hydrolyzed in an aqueous solution of potassium hydroxide in dimethyl sulfoxide for 30 minutes at 120° C. The mixture was hereafter poured on ice. Extraction with penetane and separation by chromatography on a silica gel column resulted in a 5:1 mixture of 4-methyl-bicyclo[2.2.2]oct-5-en-2-one and 1-methyl-bicyclo[2.2.2]oct-5-en-2-one in a yield of 50 to 55%.

(Analysis in %: Calculated: C, 79.41; H, 8.82; O, 11.76.

Found: C, 79.3; H, 8.9; O, 11.7).

If the same reaction was carried out at 150° C., exclusively the 1-methyl derivative was obtained in a 54% yeild. Both products were present in racemic form.

EXAMPLE 3

5.5 g. of 1-methyl-bicyclo[2.2.2]oct-5-en-2-one were refluxed together with 12 g. of L(+)-ethyl tartrate and 350 mg of p-toluene sulfonic acid in 40 ml of benzene with the use of a water separator. After a conversion of 50% was achieved, the reaction product was processed by extraction of the benzene solution with water. Concentration of the organic phase by evaporation resulted in 12 g. of raw material which was subjected to chromatography on silica gel (0.043 to 0.063 mm., 400 g.) using toluene as the solvent. The resultant mixed fractions were repeatedly subjected to chromatography. There were obtained 2.75 g. of ketal of (−)-1-methyl-bicyclo[2.2.2]oct-5-en-2-one and 1.2 g. of ketal of (+)-1-methyl-bicyclo[2.2.2]oct-5-en-2-one. Both of the enantiomers could be recovered in pure form after conventional hydrolysis of the ketals. Unreacted starting product was recovered almost quantitatively.

EXAMPLE 4

6 g. of 1-methyl-bicyclo[2.2.2]oct-5-en-2-one were refluxed together with 18 g. of L(+)-diisopropyl tartrate and 400 mg. of p-toluene sulfonic acid in 50 ml of benzene using a water separator.

At a conversion of 50%, the reaction product was processed by extraction of the benzene solution with water. Concentration of the organic phase by evaporation resulted in 14 g. of raw material which was distilled at 60° C./1.3 millibars. The distilled product consisted almost exclusively of (+)-1-methyl-bicyclo[2.2.2]oct-5-en-2-one. At 110° C./1.3 millibars, the ketal consisting of substantially pure ketal of (−)-1-methyl-bicyclo[2.2.2]oct-5-en-2-one distilled.

EXAMPLE 5

3.5 g. of racemic 4-methyl-bicyclo[2.2.2]oct-5-en-2-one were shaken with 14 g. lf L(+)-butyl tartrate and 1 g. of strongly acidic ion exchanger in 50 ml of cyclohexane for 48 hours at room temperature. After this time, 85% of the starting product had reacted. The mixture was then filtered and the filtrate washed thoroughly with water. The residue of the organic phase was subjected to chromatography with toluene on silica gel columns. After two purification passages, approximately identical amounts of the ketals of the pure enantiomers were obtained. Unreacted starting product was recovered almost quantitatively.

EXAMPLE 6

2 g. of racemic 1-butyl-bicyclo[2.2.2]oct-5-en-2-one were heated with 7 g. of D(−)-tartaric acid in 25 ml of methanol for 36 hours at 40° C. in the presence of a molecular sieve. The reaction proceeded almost quantitatively. Separation of the raw product by chromatography with ethyl acetate/methanol (2:1) on silica gel resulted in the ketals of the pure enantiomers.

EXAMPLE 7

An acetone solution (1%, 1 g.) of (−)-1-methyl-bicyclo[2.2.2]oct-5-en-2-one was degassed with argon and irradiated with a 3,000 Angstrom lamp in a water-cooled quartz vessel. After 72 hours, a conversion of 96% was measured. The acetone was distilled off and the residue subjected to chromatography on 15 g. of silica gel. Unreacted starting product was obtained with benzene and 0.86 g. of (+)-8-methyl-tricyclo[$3.3.0.0^{2,8}$]octan-3-one was obtained with benzene/ether (9:1).

(Analysis: Calculated: C, 79.41; H, 8.82; O, 11.76.
Found: C, 79.5 H, 8.8; O, 11.6).

EXAMPLE 8

A 4% solution of (+)-1-butyl-bicyclo[2.2.2]oct-5-en-2-one (1.5 g.) in cyclohexane was irradiated in a Pyrex apparatus under argon and in the presence of 200 mg. of acetophenone with a 250 w. medium pressure mercury lamp. After 50 hours, a conversion of 98% was achieved. The solution was concentrated by evaporation and the residue subjected to chromatography on 100 g. of silica gel (70 to 230 mesh) with toluene to remove the acetophenone and with toluene/1% diethyl ether. Pure (−)-8-butyl-tricyclo[$3.3.0.0^{2,8}$]octan-3-one was obtained.

(Analysis: Calculated: C, 80.9; H, 10.11; O, 8.99.
Found: C, 80.9; H, 10.0; O, 8.8).

EXAMPLE 9

A 4% solution of (+)-bicyclo[2.2.2]oct-5-en-2-one was dissolved in cyclohexane and irradiated in a Pyrex apparatus under argon with a 250 w. medium pressure mercury lamp. After 50 hours, the starting product had been reacted quantitatively. The solution was concentrated by evaporation and the residue subjected to chromatography on 100 g. of silica gel with toluene/1% diethyl ether. Pure (−)-bicyclo[4.2.0]oct-3-en-8-one was obtained.

(Analysis in %: Calculated: C, 78.69; H, 8.19; O, 13.11.
Found: C, 78.7; H, 8.2; O, 12.9).

Spectroscopic Data

1-Methyl-bicyclo[2.2.2]oct-5en-2-one

NMR: 6.38 (m, 1H) 5.72 (m, 1H) 3.2/1.3 (7H) 1.2 (s, 3H); solvent, CDCl$_3$.
IR: 3120, 3020, 2950, 1725, 1620, 1450, 1410, 1095 cm$^{-1}$ (neat).
Amount of rotation: $[\alpha]_D$ + or $-495°\pm5\%$; solvent, chloroform, 23° C.

4-Methyl-bicyclo[2.2.2]oct-5-en-2-one

NMR: 5.95 (m, 2H) 2.9/1.3 (7H) 1.27 (s, 3H); solvent, CDCl$_3$
IR: 3110, 3020, 2930, 1720, 1650, 1460, 1360, 1250, 1190, 1100 (neat).
Amount of rotation: $[\alpha]_D$ + or $-515°\pm5\%$; solvent, CHCl$_3$, 23° C.

Ketal from L(+)-ethyl tartrate and (+)-1-methyl-bicyclo[2.2.2]oct-5-en-2-one

NMR: 6.35 (m, 2H) 4.7/4.6 (dd, 2H); 4.3/4.28 (each q, each 2H) 3.1/1.5 (7H); 1.35/1.38 (each t, each 3H) 1.25 (s, 3H); solvent, CDCl$_3$.
IR: 3000, 1755, 1750, 1460, 1435, 1370, 1340, 1265, 1210, 1020 cm.$^{-1}$
$[\alpha]_D$: $-85°\pm5\%$; solvent, CHCl$_3$, 23° C.

Ketal from L(+)-ethyl tartrate and (−)-1-methyl-bicyclo[2.2.2]oct-5-en-2-one

NMR: 6.3 (m, 2H) 4.8/4.6 (dd, 2H); 4.29/4.26 (each q, each 2H) 3.1/1.5 (7H); 1.35/1.30 (each t, each 3H) 1.22 (s, 3H); solvent, CDCl$_3$.
IR: 3000, 1760, 1755, 1460, 1440, 1370, 1270, 1130, 1025 cm$^{-1}$.
$[\alpha]_D$: $+45°\pm5\%$ solvent, CHCl$_3$, 23° C.

What is claimed is:

1. A process for the preparation of a pure enantiomer of one of the formulae below

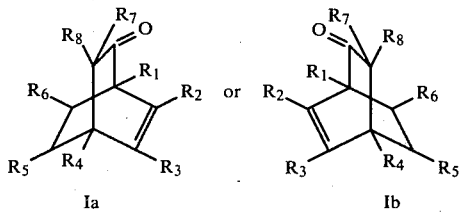

wherein
R$_1$, R$_2$, R$_3$, R$_4$, R$_5$ and R$_6$ may be H, C$_1$ to C$_8$ alkyl, C$_1$ to C$_8$ alkoxy, hydroxylated and/or carbonylated C$_1$ to C$_8$ alkyl groups which can contain one or more double and/or triple bonds and may also be —C≡N or —COOH and/or an ester thereof or

wherein R may be H, C$_1$ to C$_8$ alkyl, C$_1$ to C$_8$ alkoxy and a hydroxylated and/or carbonylated C$_1$ to C$_8$ alkyl group which can contain one or more double bonds and/or triple bonds and, moreover, the carbonyl group can be acetalized or ketalized, and
R$_7$ and R$_8$ may be H, C$_1$ to C$_8$ alkyl, C$_1$ to C$_8$ alkoxy and hydroxylated and/or carbonylated C$_1$ to C$_8$ alkyl groups which can contain one or more double bonds and/or triple bonds by effecting a Diels-Alder addition of a cyclohexadiene of the formula II or III below

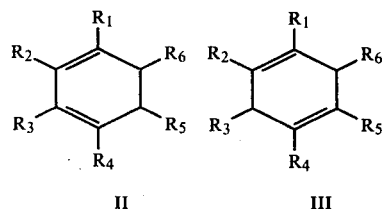

wherein
R$_1$–R$_6$ inclusive have the above-mentioned meanings with an ene of the formula

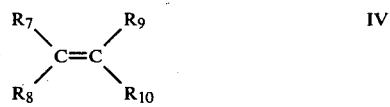

wherein
R$_7$ and R$_8$ are as defined above and
R$_9$ and R$_{10}$ are hydrolyzable substituents which are hydrolyzed under ketalization conditions, the racemates of the bicyclo[2.2.2]oct-5-ene-2-ones obtained by Diels-Alder addition are either completely ketalized with pure enantiomers of diols selected from the group consisting of 1, 3-diols; 2, 4 diols and vicinal diols and the ketals are separated by chromatography or, in the case of only partial ketalization, the enantiomeric bicyclo [2.2.2] oct-5-ene-2-one which has not been or has been less ketalized is separated from the ketalized enantiomer(s) by distillation and/or chromotography and the latter is also separated by chromotography.

2. A process according to claim 1 wherein said hydrolyzable substituents are selected from the group consisting of halogen, nitrile,

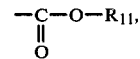

—OR$_{11}$, NO$_2$ or amino wherein R$_{11}$ is an alkyl group having 1 to 4 carbon atoms.

3. A process according to claim 1 wherein said diol is a vicinal diol.

4. A process according to claim 2 wherein said diol is a vicinal diol.

5. A process according to claim 1 wherein said diol is a 1,3- or 2,4-diol.

6. A process according to claim 2 wherein said diol is a 1,3- or 2,4-diol.

7. A process according to claim 1, characterized in that L(+)- or D(−)-tartaric acid or esters thereof are used as said diols.

8. A process for the regioselective preparation of bicyclo[2.2.2]oct-5-en-2-ones of the formulae Ia and Ib wherein R$_1$, R$_2$, R$_3$, R$_4$, R$_5$, R$_6$, R$_7$ and R$_8$ are as defined claim 1 by Diels-Alder addition of cyclohexadienes of the formulae II and III wherein R$_1$, R$_2$, R$_3$, R$_4$, R$_5$ and R$_6$ are as defined in claim 1 with enes of the formula IV wherein R$_7$ and R$_8$ are as defined above and R$_9$ and R$_{10}$ are hydrolyzable substituents, characterized in that the Diels-Alder addition is carried out in the temperature range of 60° to 120° C. or in the temperature range of 140° to 200° C. in the presence of polymerization inhibitors such as, for example, hydroquinone.

* * * * *

UNITED STATES PATENT AND TRADEMARK OFFICE
CERTIFICATE OF CORRECTION

PATENT NO. : 4415756
DATED : November 15, 1983
INVENTOR(S) : Martin Demuth and Kurt Schaffner It is certified that error appears in the above-identified patent and that said Letters Patent is hereby corrected as shown below:

Column 1, lines 60-67, delete the formula and insert therefor the formula Ia from claim 1.

Column 2, lines 1-8, delete the formula and insert therefor the formula Ib from claim 1.

Column 4, line 27, correct the formula to read -- $-\underset{\underset{O}{\|}}{C}-O-R_{11}$ --.

Column 8, line 60, before "claim 1" insert -- in --.

Signed and Sealed this

Twenty-ninth Day of May 1984

[SEAL]

Attest:

GERALD J. MOSSINGHOFF

*Attesting Officer*   *Commissioner of Patents and Trademarks*